United States Patent [19]

Quay

[11] Patent Number: 4,758,422
[45] Date of Patent: * Jul. 19, 1988

[54] FERRIOXAMINE PARAMAGNETIC CONTRAST AGENTS FOR MR IMAGING

[75] Inventor: Steven C. Quay, Menlo Park, Calif.

[73] Assignee: Salutar Inc., Los Altos, Calif.

[*] Notice: The portion of the term of this patent subsequent to Jan. 20, 2004 has been disclaimed.

[21] Appl. No.: 826,827

[22] Filed: Feb. 6, 1986

Related U.S. Application Data

[63] Continuation-in-part of Ser. No. 688,733, Jan. 4, 1985, Pat. No. 4,637,929.

[51] Int. Cl.⁴ .................. A61K 49/00; A61B 5/05; A61B 6/00
[52] U.S. Cl. ........................... 424/9; 424/1.1; 436/173; 436/806; 128/653; 128/654; 514/492; 534/10; 534/15; 556/45
[58] Field of Search ............... 424/9, 1.1; 436/173, 436/806; 556/40, 146, 147, 148, 45; 514/492; 534/10, 15; 128/653, 654

[56] References Cited

U.S. PATENT DOCUMENTS 3,471,476 10/1969 Gaeumann et al. ............. 556/146
4,647,447 3/1987 Gries et al. ...................... 424/4

FOREIGN PATENT DOCUMENTS 8633082 1/1983 Australia.

OTHER PUBLICATIONS

Yunice et al., Arch. Environ. Health, vol. 16, (1968) pp. 163-170.
Chemical Abstracts, 68: 67581n.

Primary Examiner—Robert J. Warden
Assistant Examiner—Stephen C. Wieder
Attorney, Agent, or Firm—Sprung Horn Kramer & Woods

[57] ABSTRACT

In the NMR imaging of a subject comprising administering to such subject a composition containing an image-modifying effective amount of an image enhancer, permitting the enhancer to move through the subject, and after a time interval taking an NMR image of the subject, the improvement which comprises employing as said enhancer a complex of an oxamine and a polyvalent paramagnetic metal, e.g. ferrioxamine. Novel complexes of trihydroxamic acids, optionally N-acylated, with polyvalent metals other than iron, are also described.

18 Claims, No Drawings

FERRIOXAMINE PARAMAGNETIC CONTRAST AGENTS FOR MR IMAGING

This is a continuation-in-part of Application Ser. No. 688,733 filed Jan. 4, 1985, U.S. Pat. No. 4,637,929.

The present invention relates to improvements in the enhancing of nuclear magnetic resonance imaging (MRI) of a subject, e.g. organs of a patient.

X-rays have long been used to produce images of internal organs of a patient, the patient being positioned between a source of X-rays and a film sensitive to the X-rays. Where organs (especially bones) interfere with the passage, the film is less exposed and the resulting picture, upon development of the film, is an indication of the state of the organ.

More recently, another imaging technique has been developed, viz. nuclear magnetic resonance. This avoids the harmful effects sometimes attending X-ray exposure. For improved imaging, patients could be given enhancers prior to imaging, either orally or parenterally. After a predetermined time interval for distribution of the enhancer through the patient, the image could be taken. The time of good imaging is desirably as short as possibly after taking the enhancer; on the other hand there is a decay in effectiveness so desirably the decay is relatively slow so as to provide a substantial time interval during which imaging can be done.

Australian Application No. AU-A-86330/82 of July 22, 1982 discloses use as an NMR image enhancer of a complex salt, preferably the gadolinium chelate of diethylenetriaminepentaacetic acid plus two mole equivalents of an amine. From the data reported therein these appear to perform well. However, gadolinium is expensive, is foreign to the body, and is reported to present some potential problems if administered to humans. Moreover, an amine is also required.

It is accordingly an object of the present invention to provide alternative image enhancers which avoid one or more of the aforementioned disadvantages.

These and other objects and advantages are realized in accordance with the present invention pursuant to which the image enhancer comprises a complex of an oxamine and a polyvalent, preferably trivalent, paramagnetic metal.

While lanthanides and particularly gadolinium are highly paramagnetic and useful in accordance with the invention, it is surprising that other less paramagnetic metals perform substantially equally well, e.g. manganese, copper, cobalt and especially iron.

The oxamine is advantageously a trihydroxamic acid, especially of the formula

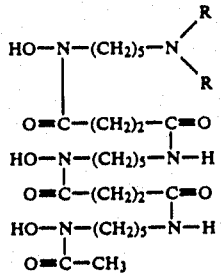

in which

R each independently is hydrogen, $C_{1-18}$-alkyl, $C_{3-8}$-cycloalkyl, $C_{1-18}$-alkyl-CO- or $C_{3-8}$-cycloalkyl-CO-.

Trihydroxamic acid of the foregoing formula in which R is hydrogen is commercially available in the form of its iron free form known as desferrioxamine (Desferal TM) and being sold by Ciba-Geigy Corporation, 556 Morris Avenue, Summit, N.J. 07901.

This material can be used as a source for image enhancers. Thus, one can form ferrioxamine mesylate (see example) and use it directly. Similarly, if a complex with another metal is desired, the desferrioxamine can be dissolved in water along with a solution of the desired ion, such as manganese chloride. The solution can thereafter be used per se or can be dried to yield a dry solid for later dissolution and use.

Where R is other than hydrogen, the radical is introduced by alkylation or acylation in known manner, e.g. reaction with an alkylating agent such as an alkyl halide (chloride, bromide or iodide) or sulfate or diazo-derivative. For acylation, acyl halides and anhydrides have proven useful. To prevent undesired reaction at some other site on the molecule, e.g. the hydrogen of the —N—OH moiety, the oxamine should first be complexed with the polyvalent metal, whereby such other sites are effectively blocked during alkylation or acylation (Example 2 hereinbelow). Thereafter the metal can be removed or replaced, if desired.

In accordance with another aspect of the invention, the pH of the aqueous solution of the complex, which is about 1 when made from des-ferrioxamine and an equimolar amount of ferric chloride, is brought up to about 4 to 6 and preferably 4.5 to 5.5. Lower pH's are not suitable for administration. A higher pH such as 7 results in reduced shelf life and storage stability, i.e. in time solid particles settle out presumably due to hydrolysis.

The solution of complex may be sterilized and made up into ampules or may be lyophilized into a powder for dissolution when ready to be used. The solution may be mixed with conventional additives such as saline solution, albumin, buffers and the like. If desired, ampules may be made up containing lyophilized powder of the complex in one compartment and a solution of additives in another separated from the first by a frangible barrier. When ready to use, the barrier is broken and the ampule shaken to form a solution suitable for use.

Immediately prior to actual administration of the contrast agent, the reconstituted solution may be administered directly or can be further diluted by addition of at least 100 ml (up to 1000 ml) of a suitable diluent such as;

Sodium Chloride Injection, USP
Dextrose Injection, USP (5 percent Dextrose in sterile water)
Dextrose Sodium Chloride Injection, USP (5 percent Dextrose in Sodium Chloride)
Lactated Ringer's Injection, USP
Protein Hydrolysate Injection
  Low Sodium, USP 5 percent
  5 percent with Dextrose 5 percent
  5 percent with Invert Sugar 10 percent The manner and dosage of administration and the manner of scanning are substantially the same as in the prior art. With solutions containing about 50 to 200 mmoles of the complex liter, sufficient solution should be administered orally or parenterally to provide about 1 to 100 umols/kg, corresponding to about 1 to 50 mmol for an adult human patient.

For smaller patients or other animals, the dosage should be varied accordingly. The particular complex and organ to be imaged will determine the waiting period between administration and imaging. The waiting period can be as short as 2 seconds and as long as about one hour.

The presence of long chain olephilic residues such as palmitoyl slow down the movement to the kidneys due to temporary entrapment or enrichment in organs which have efficient fatty acid uptake systems such as the hepatobiliary system. Thus, such acylates are especially useful for liver imaging. Other organs such as the kidney, ureter, bladder, brain and heart can be imaged well with the lower homologues or non-acylated complexes. Since the complexes do not penetrate the blood-brain-barrier under normal circumstances they are useful in detecting the extravasation of arterial blood in the extravascular space during cerebral hemorrhaging and in the edema fluid surrounding tumors.

As noted, iron is the preferred metal but other polyvalent paramagnetic metals may be used, e.g. manganese, chromium, cobalt, nickel, copper, and the like. The preferred lanthanide is gadolinium, but others such as lanthanum, cerium, praseodymium, neodymium, promethium, samarium, europium, terbium, dysprosium, holmium, erbium, thulium, ytterbium and lutetium may also be used.

The images can be taken in conventional manner using any of the machines currently available, e.g. those of Elscint, Toshiba, Siemens AG of Erlanger, Federal Republic of Germany, General Electric, Diasonics, Technicare, Fonar, Resonix and Accuscan.

Further details of imaging systems are described in the prior art, e.g. 'NMR A Primer for Medical Imaging' by Wolf and Popp Slack Book Division (ISBN 0-943432-19-7) and Scientific American, May 1982, pages 78-88.

The invention will be further described in the following illustrative examples wherein all parts are by weight unless otherwise expressed.

EXAMPLE 1

Formation of Ferrioxamine Mesylate (a) Desferrioxamine mesylate (450 gm; Ciba-Geigy Corporation, Summit, N.J.) was added to 1260 ml of water for injection and stirred until dissolved. To another container, ferric chloride hexahydrate (185.2 gm; Aldrich Chemical Co., Milwakee, Wis.) was added to 148 ml of water and dissolved. When dissolution was complete, the ferric chloride solution was slowly added to the desferrioxamine solution with stirring. A dark red solution was formed with a pH of less than 2.0. Stirring was continued for an additional 15 minutes.

Using a 5.0 N sodium hydroxide solution the pH was carefully adjusted towards neutrality, care having been taken to avoid over shooting the pH by a large amount since precipitation might have been induced.

(b) The long range stability is surprisingly sensitive to the final solution pH. Table 1 shows the stability data of two separate lots at low (4.87) or neutral (7.47) pH values.

TABLE 1

The effect of the final ph on the number of particulates found in the final product after 3 weeks standing

| Final sol'n pH, Temp. | Particulates per 8 ml vial | | | |
|---|---|---|---|---|
| | 0–25µ | 25–50µ | 50µ | Total |
| 4.87, 40° C. | 11 | 1 | 3 | 15 |
| 4.87, 50° C. | 25 | 1 | 2 | 28 |
| 7.47, 40° C. | 237 | 35 | 66 | 338 |
| 7.47, 50° C. | Totally precipitated (red color) | | | |

The pH 4.87 material has 4% of the particulates of the neutral pH material.

(C) After the pH in (a) was adjusted the volume was brought up with water for injection to give a final concentration of 200 mg/ml. The material was then filter sterilized and added to vials.

EXAMPLE 2

Manganese Desferrioxamine Mesylate

By replacing the ferric chloride hexahydrate in Example 1(a) by the equivalent amount of manganese chloride $MnCl_2.4H_2O$, the named product was obtained by the process of Example 1(a) and (c).

EXAMPLE 3

Formation of Valeryl Ferrioxamine mesylate

Ferrioxamine mesylate formed as in Example 1, was rendered a dry powder by vacuum evaporation on a Buchi model RE120 rotary evaporator, and 0.54 gm (0.761 mmols) was added to 30 ml of water and the pH adjusted to 8.50 with NaOH. Separately, 0.3 ml of valeryl chloride (2.53 mmols; 3.3-fold excess; Aldrich Chemical Company) was dissolved in chloroform. With the ferrioxamine mesylate stirring vigorously, the valeryl chloride solution was added dropwise. The pH dropped as the reaction proceeded and 0.6 N NaOH was added to maintain the pH between 8 and 9. The addition of the valeryl chloride took about 20 minutes. The pH stabilized about 45 minutes after the addition of valeryl chloride was completed.

The product solution was washed with 50 ml chloroform to remove excess valeryl chloride and valeric acid and then extracted with n-butanol. The n-butanol solution was subjected to rotary evaporation and the elemental analysis agreed with theoretical (Galbraith Laboratories) for valeryl ferrioxamine mesylate.

EXAMPLE 4

Use of Ferrioxamine mesylate as a NMR contrast agent

A 200 mg/ml solution of ferrioxamine mesylate (Example 1(c)) was administered to a human subject at a dosage of 20 mg/kg body weight (8.25 ml) by fast intravascular injection into a dorsal hand vein. The subject was supine and in place in the bone of a GE 1.5 Tesla MR imager. Images were taken continuously for 15 minutes using a partial saturation imaging technique (TE=25 msec; TR=300 msec; 2 averages). Both the kidneys and the bladder showed substantial image enhancement as early as 90 seconds after injection.

It will be understood that the specification and examples are illustrative but not limitative of the present invention and that other embodiments within the spirit and scope of the invention will suggest themselves to those skilled in the art.

I claim:

1. A complex of a des-ferrioxamine and a metal selected from the group consisting of a lanthanide and manganese.

2. A complex according to claim 1, wherein the metal is selected from the group consisting of gadolinium and manganese.

3. A complex according to claim 1, wherein the des-ferrioxamine is a trihydroxamic acid.

4. A complex according to claim 1, wherein the des-ferrioxamine is of the formula

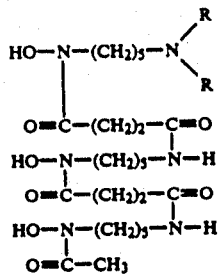

in which
R each independently is hydrogen, $C_{1-18}$-alkyl, $C_{3-8}$-cycloalkyl, $C_{1-18}$-alkyl-CO- or $C_{3-8}$-cycloalkyl-CO-.

5. A complex according to claim 4, in which R each independently is hydrogen or $C_{12-18}$-alkyl-CO-.

6. A composition for modifying the relaxation times in NMR imaging, comprising an amount effective therefor of a complex according to claim 1 and a physiologically acceptable carrier.

7. A stable aqueous solution of a complex of a des-ferrioxamine and a polyvalent paramagnetic metal selected from the group consisting of a lanthanide and manganese, containing alkali in amount sufficient to bring the pH to about 4 to 6.

8. A solution according to claim 7, wherein the pH is about 4.5 to 5.5.

9. A solution according to claim 7, wherein the metal is selected from the group consisting of gadolinium and manganese, and the des-ferrioxamine is a trihydroxamine acid.

10. A solution according to claim 9, wherein the des-ferrioxamine is of the formula

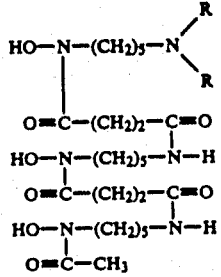

in which
R each independently is hydrogen, $C_{1-18}$-alkyl, $C_{3-8}$-cycloalkyl, $C_{1-18}$-alkyl-CO- or $C_{3-8}$-cycloalkyl-CO-.

11. A solution according to claim 10, wherein the metal is iron and R each independently is hydrogen or $C_{12-18}$-alkyl-CO-.

12. A process for making a complex of a polyvalent metal and an N-substituted oxamine of the formula

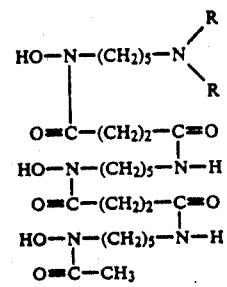

in which
R each independently is $C_{1-18}$-alkyl, $C_{3-8}$-cycloalkyl, $C_{1-18}$-alkyl-CO- or $C_{3-8}$-cycloalkyl-CO-, and one R may be hydrogen
which comprises reacting an oxamine of the formula

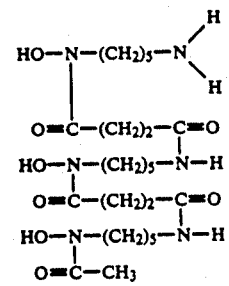

with a salt of the polyvalent metal thereby to form a complex of the polyvalent metal and the oxamine acid, and thereafter reacting said complex with an acylating or alkylating agent to replace H by R.

13. A process according to claim 12, wherein the polyvalent metal is iron and the complex is reacted with an acid halide or anhydride of an acid of the formula $C_{1-18}$-alkyl-COOH.

14. In the NMR imaging of a subject comprising administering to such subject a composition containing an image-modifying effective amount of an image enhancer, permitting the enhancer to move through the subject, and after a time interval taking an NMR image of the subject, the improvement which comprises employing as said enhancer a complex of an oxamine and a polyvalent paramagnetic metal.

15. A process according to claim 14, wherein the metal is selected from the group consisting of gadolinium, manganese, copper, cobalt and iron, and the oxamine is a trihydroxamic acid.

16. A process according to claim 15, wherein the oxamine is of the formula

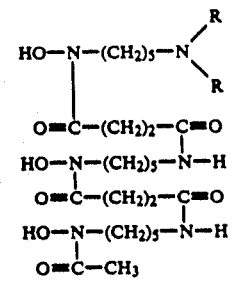

in which
R each independently is hydrogen, $C_{1-18}$-alkyl, $C_{3-8}$-cycloalkyl, $C_{1-18}$-alkyl-CO- or $C_{3-8}$-cycloalkyl-CO-.

17. A process according to claim 16, wherein the metal is iron and R each independently is hydrogen or $C_{12-18}$-alkyl-CO-.

18. A process according to claim 17, wherein at least one R is $C_{12-18}$-alkyl-CO- and the imaging is of an organ of the hepatobiliary system of the subject.

* * * * *

UNITED STATES PATENT AND TRADEMARK OFFICE
CERTIFICATE OF CORRECTION

PATENT NO. : 4,758,422

DATED : July 19, 1988

INVENTOR(S) : Steven C. Quay

It is certified that error appears in the above-identified patent and that said Letters Patent is hereby corrected as shown below:

Col. 5, lines 42-43      Delete "trihydroxamine" and sub-
(Claim 9)                    stitute --trihydroxamic--

Signed and Sealed this

Twenty-eighth Day of February, 1989

Attest:

DONALD J. QUIGG

Attesting Officer      Commissioner of Patents and Trademarks